(12) United States Patent
Obrebski et al.

(10) Patent No.: US 7,307,785 B2
(45) Date of Patent: Dec. 11, 2007

(54) MICROSCOPY SYSTEM FOR EYE SURGERY AND METHOD OF ILLUMINATION

(75) Inventors: Andreas Obrebski, Duesseldorf (DE); Christoph Hauger, Aalen (DE); Peter Reimer, Ellwangen (DE); Ludwin Monz, Mainz (DE); Bernd Spruck, Moeggilngen (DE); Alfons Abele, Schw. Gmuend (DE); Hans Adolf Von Derschau, Oberkochen (DE); Gerhard Möller, Aalen (DE); Peter Amend, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 96 days.

(21) Appl. No.: 10/768,700

(22) Filed: Feb. 2, 2004

(65) Prior Publication Data

US 2004/0227989 A1 Nov. 18, 2004

(30) Foreign Application Priority Data

Feb. 3, 2003 (DE) ................................ 103 04 267

(51) Int. Cl.
*G02B 21/06* (2006.01)
*A61B 18/18* (2006.01)

(52) U.S. Cl. ............................ 359/389; 359/388; 606/4

(58) Field of Classification Search ................ 359/368, 359/385–389; 606/4, 6; 351/205, 221, 246
See application file for complete search history.

(56) References Cited

U.S. PATENT DOCUMENTS 4,638,801 A    1/1987  Daly et al.
4,715,704 A   12/1987  Biber et al.
4,783,142 A   11/1988  Mutzhas
4,786,155 A   11/1988  Fantone et al.
4,991,947 A    2/1991  Sander et al.
5,206,672 A *  4/1993  Rowe ......................... 351/212
5,733,739 A    3/1998  Zakim et al.
5,751,396 A *  5/1998  Masuda et al. ............. 351/221
5,760,952 A    6/1998  Koetke
5,856,883 A    1/1999  Sander
5,865,829 A    2/1999  Kitajima
5,943,118 A    8/1999  Koschmieder et al.
6,002,476 A   12/1999  Treado
6,005,709 A   12/1999  Silver
6,028,707 A    2/2000  Ganswein et al.
6,031,619 A    2/2000  Wilkens et al.
6,243,197 B1   6/2001  Schalz (Continued)

FOREIGN PATENT DOCUMENTS

DE           34 24 995         1/1985

(Continued)

OTHER PUBLICATIONS

Dillon, J., "UV-B as a pro-aging and pro-cataract factor", Medin, Documenta Ophthalmologica, (1994-95) 88 (3-4) 339-44 (ABSTRACT).

*Primary Examiner*—Alessandro Amari
(74) *Attorney, Agent, or Firm*—Potomac Patent Group PLLC

(57) ABSTRACT

A microscopy system for eye surgery with an objective lens is suggested, which provides a retroillumination system to generate a so-called red reflex illumination during an eye-surgical treatment, in particular during a cataract operation.

30 Claims, 13 Drawing Sheets

U.S. PATENT DOCUMENTS

| | | | |
|---|---|---|---|
| 6,267,477 B1 * | 7/2001 | Karpol et al. | 351/221 |
| 6,309,070 B1 * | 10/2001 | Svetliza et al. | 351/221 |
| 6,914,721 B2 * | 7/2005 | Deverin et al. | 359/388 |
| 2002/0087149 A1 | 7/2002 | McCary | |
| 2002/0113941 A1 | 8/2002 | Bees | |

FOREIGN PATENT DOCUMENTS

| | | |
|---|---|---|
| DE | 33 39 172 | 5/1985 |
| DE | 35 32 780 | 3/1987 |
| DE | 40 28 605 | 3/1992 |
| DE | 42 14 445 | 11/1993 |
| DE | 42 14 445 A1 | 11/1993 |
| DE | 43 20 579 | 12/1993 |
| DE | 43 31 635 | 6/1994 |
| DE | 196 50 773 | 7/1997 |
| DE | 196 44 662 | 4/1998 |
| DE | 198 12 050 | 9/1999 |
| DE | 101 08 254 | 8/2002 |
| EP | 0 611 547 | 8/1994 |
| EP | 0 898 183 | 2/1999 |
| EP | 1 235 093 | 8/2002 |
| GB | 2 249 193 | 4/1992 |
| JP | 2001-017459 | 1/2001 |
| WO | WO1997/046903 | 12/1997 |
| WO | WO 1999/007306 | 2/1999 |
| WO | WO 2000/006980 | 2/2000 |

* cited by examiner

MICROSCOPY SYSTEM FOR EYE SURGERY AND METHOD OF ILLUMINATION

This application claims the benefit of priority application DE 103 04 267.9 filed in Germany on Feb. 3, 2003. The subject matter of both of these applications is incorporated herein by reference.

BACKGROUND OF THE INVENTION

1. Field of the Invention

The invention relates to a microscopy system for eye surgery to support a surgeon performing a surgical eye treatment, and the invention relates to a method of illuminating the eye under surgery.

In particular the microscopy system is configured to provide an appropriate illumination for a treatment of a region of the eye, such as a cornea, an iris, and a lens of the eye. A possible application of the microscopy system is a cataract surgery, where a natural lens of the human eye, in which a cataract has developed, is to be substituted by an artificial lens.

2. Brief Description of Related Art

In the following a conventional microscopy system for eye surgery is explained with reference to FIGS. 1 to 3:

FIG. 1 schematically illustrates a beam path of a microscopy system 1. The microscopy system 1 comprises an objective lens 3 with an optical axis 5 and an object plane 7, in which a region of the eye under surgery is arranged. The objective lens 3 transforms a beam 11 on an object side and emerging from the object plane 7 into an angle 9 about the optical axis 5 to infinity, and transforms the beam 11 to a beam 13 on the image side.

In the beam 13 on the image side, two zoom systems 15, 16, each having an optical axis 17 and 18, respectively, are arranged adjacent to each other such that their optical axes 17, 18 are displaced in parallel to the optical axis 5 of the objective lens 3 and arranged with a distance a from each other. Each of the zoom systems 15, 16 receives a partial beam 19 and 20, respectively, of the beam 13. The partial beam 19 is supplied to a left eye 21 of the surgeon, and the other partial beam 20 is supplied to the right eye 22 of the surgeon. A lens 23 of a tube, a prism system 25 and an ocular 27 are arranged in the beam path of the partial beams 19, 20. The left eye 21 perceives the object plane 7 inclined by a perspective angle $\alpha$ with respect to the optical axis 5. The right eye 22 perceives the object plane 7 inclined by a perspective angle $-\alpha$ with respect to the optical axis 5. Thereby, the surgeon obtains a stereoscopic impression of the region of the eye under surgery and arranged in the object plane 7.

For example, for removing the natural lens during a cataract operation it is necessary to remove the lens completely by sucking it off. It turned out that remaining portions of the lens of the eye are well visible to the surgeon when a retroillumination is employed which is sometimes also referred to as a red reflex illumination. Herein, light is emitted from an objective lens 3 side of the microscope through the pupil 32 (see FIG. 2) and through the lens 33 of the eye into an inside of the eye 31, and the light is incident on the retina 34 and the eye fundus, respectively. There the irradiated light is reflected and illuminates the lens 33 of the eye and the remaining portions of the lens from the backside, thus facilitating their visibility. Herein, the retina reflects substantially only red light, so that the lens 33 of the eye or its remaining portions appear in a red light, from which the designation red reflex illumination is derived.

FIGS. 2 and 3 show an arrangement of a retroillumination device 35 used for generating the red reflex.

The top view of FIG. 3 shows the zoom systems 15, 16 and centers 36 of beams 20 entering the zoom systems at a plane of an objective lens 3. In addition, FIG. 3 shows a connecting line 38 between the centers 36 in a plane of the objective lens 3. This connecting line 38 is arranged with a distance from the optical axis 5 such that in the side view according to FIG. 2, main rays of the partial beams 19, 20 extend under an angle $\delta$ with respect to the optical axis which may also be zero.

Light of a light source, not shown in FIG. 2, is supplied by an illumination system 35 via an optical fiber 37; the light is expanded by a collimation optic 39 and formed to a parallel beam 40. A mirror 41 is arranged with a distance from the optical axis 5 of the objective lens 3 and directs a partial beam of the beam 40 generated by the collimation optic 39 such that this partial beam extends in parallel to the optical axis 5 of the objective lens 3 and traverses the objective lens 3. Thus, as seen in the side view of FIG. 2, a main ray of the partial beam enters the eye 31 under an angle $\beta$ of about 2° with respect to main rays of the observation beams 19, 20 as a beam of retroillumination light 43; and, as indicated in FIG. 2 by the arrows 34, the partial beam is reflected there and generates the retroillumination and the red reflex, respectively. The angle $\beta=2°$, specified above, is exemplary. Other angles as those between $-2°$ and $+2°$ have proven favorable.

In addition to the beam of retroillumination light 43, a main ray of a beam of standard illumination light 45 is incident on the object plane 7 under a greater angle $\epsilon$ of about 7° to the plane of main rays of the observation beams 19, 20. A mirror 47 generates the beam of standard illumination light 45 by redirecting the light beam 40, provided by the collimation optic 39. The beam of standard illumination light serves as the usual illumination of the object plane 7 and herewith of the region of the eye 31, at which the treatment is carried out. The beam of standard illumination light 45 illuminates those regions of the eye which are arranged in the object plane 7, such as the iris, such that these regions may be well perceived by the surgeon. The beam of standard illumination light does substantially not contribute to generation of the red reflex. The beam of standard illumination light 45 serves for the illumination of the object plane with an illumination light well facilitating the usual visual observation, without contributing substantially to the generation of a red reflex; in particular the illumination light lets the objects, which are arranged in the object plane, appear in true colors. The mirror 47 comprises a cutout 49 for light penetration to the mirror 41.

In practice, generating the red reflex and maintaining the red reflex during the surgical treatment, especially when the eye is moving, or the lens is changed, is often involving a considerable effort. Further attention has to be paid that for protection of the retina of the eye an intensity of the retroillumination has to be limited so that the red reflex cannot always be generated with the desired intensity.

SUMMARY OF THE INVENTION

It is an object of the present invention to provide a microscopy system for eye surgery, which facilitates at least one of generating the red reflex, and limiting a stress on the retina of the eye under surgery, while generating an intense red reflex.

Herein, the invention relates to a microscopy system for eye surgery, the microscopy system comprising an objective lens for imaging an object plane of the objective lens, and a retroillumination system for generating at least one beam of retroillumination light directed towards the object plane from an objective lens side of the object plane.

According to a first aspect of the invention, the microscopy system for eye surgery is configured such that the beam of retroillumination light substantially comprises only visible light from a wavelength range greater than 540 nanometers, and in particular greater than 600 nanometers. According to an embodiment, the light of the retroillumination is at least one of red light and infrared light.

Herein, one underlying consideration is that the retina of the eye reflects mainly red light, which generates the retroillumination. Thus, the retina absorbs light of other colors, which contribute to a thermal stress on the retina rather than generating the red reflex. For generating an intense red reflex, only red light is irradiated into the eye, and an unnecessary stress on the retina by light of other colors is avoided. The irradiated red light is from a wavelength range which is effectively reflected by the retina. This does not exclude that the beam of retroillumination light contains light outside of this wavelength range. However, this should be the case only for a small part of the light, in particular a part of less than 60%. Preferably more than 50% of the light intensity of the beam of retroillumination light is within a wavelength range from 530 nanometers to 780 nanometers.

Preferably, the wavelength range of the beam of retroillumination light can be matched to an eye under surgery. It has been found that a wavelength dependency of the reflectivity of the retina differs between individuals, wherein the wavelength dependencies are especially different between the individuals of different ethnic groups. E.g. the wavelength dependency of the reflectivity of the retina can be measured in advance, and then the wavelength band used for the beam of retroillumination light, can be matched to the determined reflectivity of the retina, with regard to an optimization of the retroillumination.

The beam of retroillumination light is preferably generated by an appropriate light source, in particular a red light source, or by use of an appropriate color filter. According to an embodiment, the filter is disposed in a beam path of the retroillumination system, and the filter is non-transparent for light other than red light. According to a further embodiment, a mirror configured to reflect substantially only red light may also form this filter. The light source may comprise a light emitting diode (LED), in particular an organic light emitting diode (OLED), a laser, in particular a semiconductor laser, and any other type of light source.

According to an embodiment, the light source generates light having a broad spectrum, and a frequency-selective beam splitter is provided, which splits the light beam, generated by the light source, into a beam of standard illumination light and a beam of retroillumination light. A main ray of the beam of standard illumination light and a main ray of the beam of retroillumination light extend under different angles with respect to a plane, in which the main rays of observation beams of the microscope are arranged, wherein the angle of the beam of retroillumination light is smaller than the angle of the beam of standard illumination light.

According to a further aspect of the invention, the retroillumination system comprises a plurality of light sources, each for generating one beam of retroillumination light.

Herewith several beams of retroillumination light can be generated, wherein a main ray of each of the beams extends under a different angle towards a plane, in which the main rays of observation beams are arranged. At least one of the beams of retroillumination light enters the operated eye such that an appropriate red reflex is generated. Preferably the light sources can be switched on and off separately, for switching off those light sources, which do not contribute or contribute only a little to the generation of the red reflex during the configuration of the eye occurring during the operation. This in turn facilitates reducing the stress on the retina.

According to an embodiment, the light sources are arranged in a source plane along at least a portion of a circle.

Herein it is possible to arrange the circle circumferentially around an observer's pupil, i.e. around such a partial beam of the light beam on the image side which is selected by a zoom system or an ocular system for generating an image of the object plane for the user.

Further, it is possible to arrange the light sources in a source plane substantially uniformly, e.g. in a grid pattern.

As an alternative to the possibility of providing a plurality of light sources, it is also preferred to provide a light source having a light beam which is incident on a plurality of switchable light valve elements. The switchable light valve elements selectively block or allow the light to pass therethrough, for selectively generating beams of retroillumination light. In an embodiment, the light valve elements are configured to reflect the beams of retroillumination light.

According to an embodiment, a controller is provided selectively controlling a plurality of light sources and a plurality of light valve elements, respectively, such that only those beams of retroillumination light are switched on which traverse the object plane within selected regions.

According to a further aspect of the invention, the microscopy system for eye surgery is configured such that a cross section of the beam of retroillumination light is displaceable in a plane disposed in-between the objective lens and the object plane.

Thereby, it is possible to change an angle between a main ray of the beam of retroillumination light and a plane in which main rays of the observation beams of the microscope are arranged. Thus, the generation of the red reflex can be maintained even when the configuration of the eye under surgery varies during the surgical treatment.

According to an embodiment, a mirror for redirecting the beam of retroillumination light is disposed in a plane between the objective lens and the object plane and is displaceable in directions transverse to the optical axis of the objective lens. Further, it is possible to arrange the light source for generating the beam of retroillumination light such that it is displaceable in directions transverse to the optical axis of the objective lens.

According to an embodiment, there is provided a light color sensor for detecting light emerging from the object plane. The light color sensor generates a color signal representing a color of the detected light. A controller analyzes the color signal and determines a location of a cross section of the beam of retroillumination light in dependence of the color signal.

According to a further aspect, the invention provides a retroillumination system, which comprises a collimator for changing a convergence or divergence of the beam of retroillumination light. Thereby, it is possible to focus the beam of retroillumination light such that the beam becomes a small spot on the retina of the operated eye. It has been found that the red reflex generates a retroillumination with a high contrast, if the spot on the retina, on which the beam of retroillumination light is incident, is relatively small. Due to the variability of the convergence or divergence, respectively, of the beam of retroillumination light, such small spot can be generated even when the natural lens has not yet been removed and the eye is near-sighted or far-sighted. Further, when the lens of the eye has been removed, the convergence or divergence, respectively, of the beam of retroillumination light can also be adapted such that a small spot on the retina is illuminated.

According to an embodiment, a controller is provided to control the collimator for changing the convergence or divergence, respectively, with regard to an optimal retroillumination. Further, a camera may be provided, which derives an image of the object plane. The controller may then adjust the collimator in dependence of a contrast of the image captured by the camera.

According to a further aspect the invention provides a method of generating a retroillumination in an eye.

BRIEF DESCRIPTION OF THE DRAWINGS

The foregoing as well as other advantageous features of the invention will be more apparent from the following detailed description of preferred embodiments of the invention with reference to the accompanying drawings. Herein.

Figure 1:
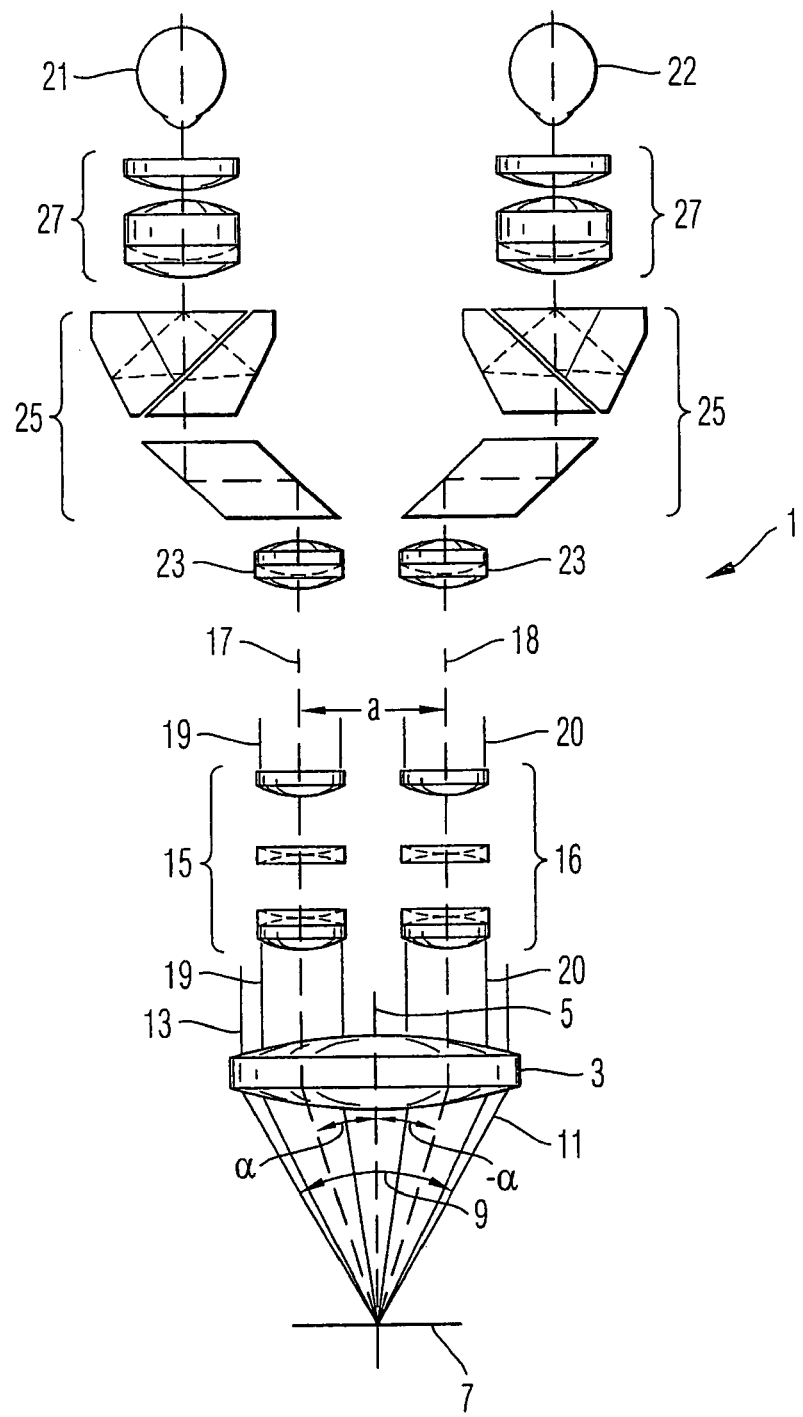
FIGS. 1, 2, 3 show a schematic representation of a conventional microscopy system for eye surgery.
Figure 4:
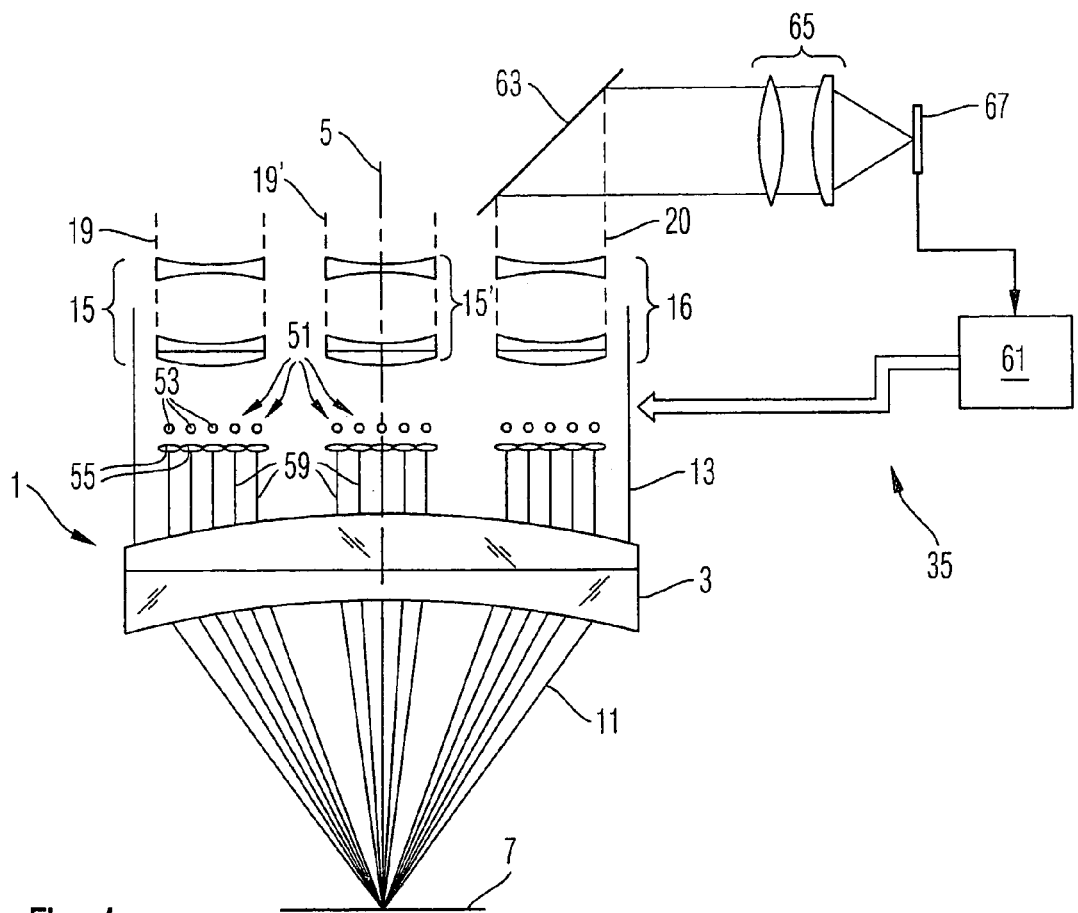
FIGS. 4, 5 show schematic representations of a portion of a microscopy system for eye surgery according to a first embodiment of the invention.
Figure 5:
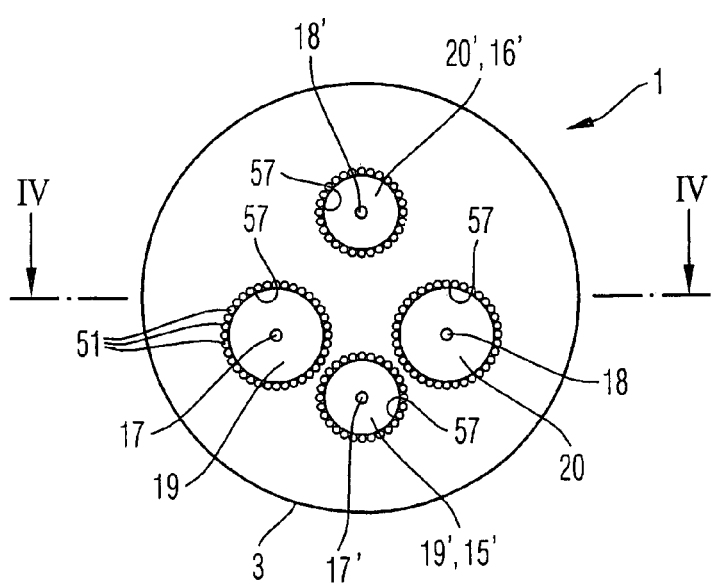

A microscopy system for eye surgery 1, shown in the schematic detailed representations of FIGS. 4 and 5, provides an arrangement, which is similar to the conventional system, shown in FIG. 1. An objective lens 3 is provided for transforming a ray bundle 11, emerging from an object plane 7, into a ray bundle 13 on an image side.

Within the ray bundle 13, two zoom systems 15, 16 are disposed, each of which selecting an observation ray bundle 19, 20, respectively, out of the ray bundle 13 for supplying the observation ray bundle 19, 20 to an ocular, not shown in FIG. 4 for observation by a first surgeon. In addition to the zoom systems 15 and 16, there are provided two further zoom systems 15', 16', each for selecting an observation ray bundle 19', 20', respectively, out of the ray bundle 13 and for supplying the observation ray bundles to oculars for a second surgeon. Thus two surgeons may look into the microscopy system for viewing an image of an eye under surgery.

A plurality of light sources 51 is arranged between the zoom systems 15, 16, 15' and 16' and the objective lens 3, each comprising a light emitting diode 53 and a collimating micro lens 55. In a plane oriented transverse to the optical axis 5 of the objective lens 3, the light sources 51 are arranged along circular lines 57 which surround optical axes 17, 18, 17' and 18' of the observation ray bundles 19, 20, 19' and 20', respectively.

Each of the light emitting diodes 53 emits red light, collimated by collimating micro lenses into substantially parallel beams of retroillumination light 59 extending towards the objective lens 3 and in parallel to the optical axis 5. The objective lens 3 is redirecting the beams of retroillumination light such that they converge towards the optical axis 5 within the ray bundle 11 on the object side and substantially intersect with each other at object plane 7. At the object plane, the beams enter the operated eye via the pupil of the eye and are incident on the retina of the eye for generating the red reflex. The light emitting diodes 53 emit only red light in order to reduce the thermal stress on the retina of the eye.

Further, a controller 61 is provided for switching the individual light sources 51 on and off.

Controller 61 facilitates switching on and off the light s sources 51 individually, and particularly in groups. Thus, particularly those groups of light sources 51 can be switched off which are arranged around a partial ray bundle, which is actually not used for observation by any of the surgeons.

Further, it is possible to switch off light sources 51 at sections of the circles 57, for achieving a retroillumination with a higher contrast. A semi-transparent mirror 63 is arranged within the beam path of each partial ray bundle 19, 20, 19', 20' for coupling a partial ray out of the respective partial ray bundle which is used to generate an image of the object plane 7 on a CCD chip 67 via a camera optics 65. The controller 61 reads the image information from the camera chip 67 and analyzes the image captured by the camera chip 67. Then the controller 61 selectively switches off some of the light sources 51 for optimizing the image captured by camera 67 with regard to achieving a better red reflex.

In the following, variants of the embodiments explained with reference to the FIGS. 1 to 5 are described. In the variants described below, components having corresponding functions and structures are designated by the same reference numerals supplemented by an additional character. To understand the features of the individual components of a specific embodiment, the descriptions of other embodiments should be referred to.

Figure 6:
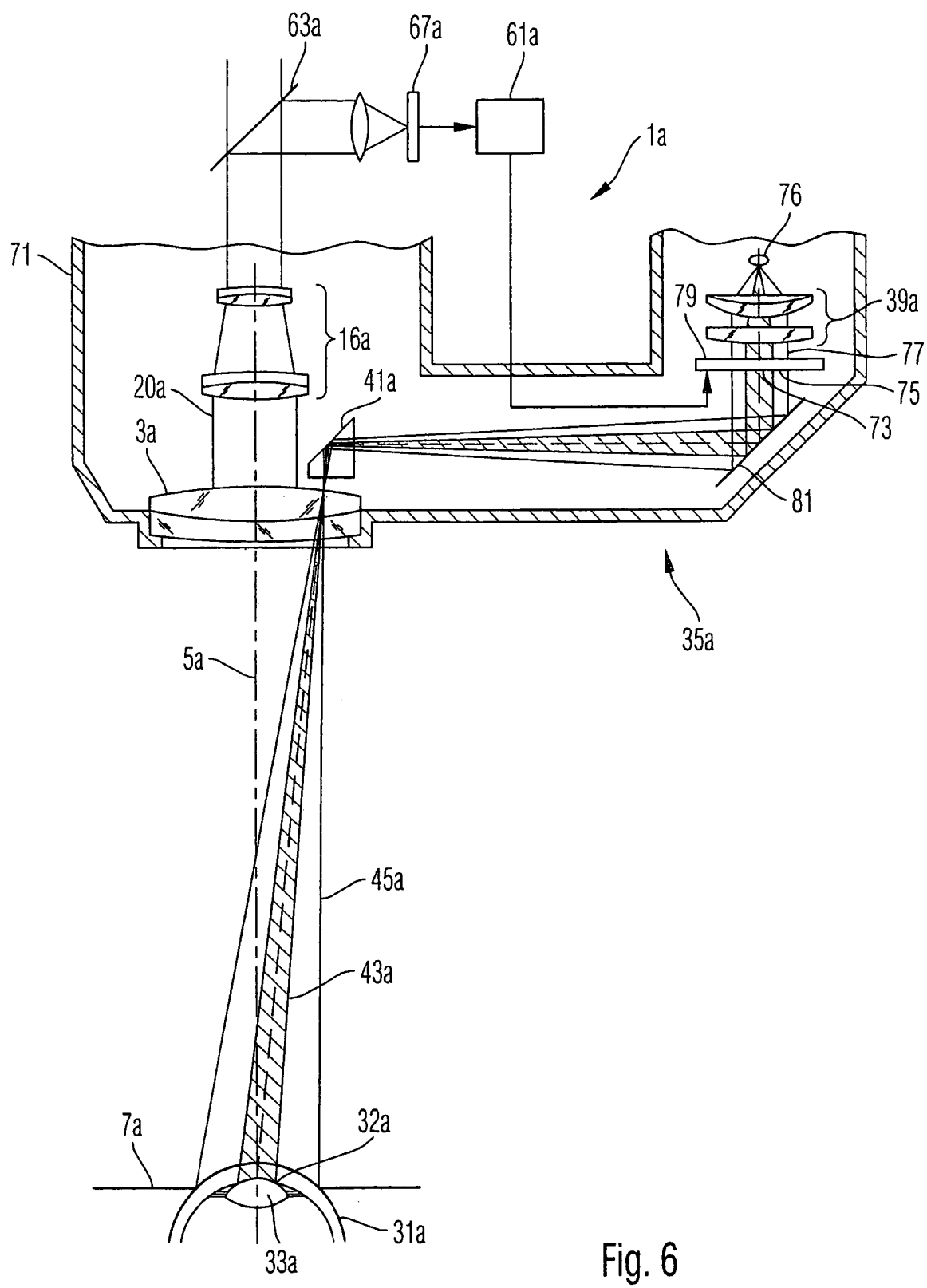
FIG. 6 shows a schematic representation of a microscopy system for eye surgery according to a second embodiment of the invention.

A microscopy system for eye surgery, partially shown in a schematic sectional representation of FIG. 6, comprises an objective lens 3a and zoom systems 16a disposed within a housing 71. An illumination system 35a provides a beam of retroillumination light 43a for generating a red reflex and a beam of standard illumination light 45a for illumination of an object plane 7a of objective lens 3a with standard light. The illumination system 35a comprises a white light source 76 emitting light and a collimation optic 39a for forming a slightly collimated beam 77.

The light beam 77 traverses an LCD array 79 having switchable liquid crystal elements, each selectively transmitting one of the colors red, green and blue. In a central region 73 of the liquid crystal array 79, the elements are switched such that only red light is transmitted. In a ring-shaped region 75 arranged around the central region 73, the elements are switched such that light of the colors red, green and blue is transmitted, i.e. altogether white light is transmitted. FIG. 6 shows the beam of red light transmitted via the central region 73 as a hatched area. Having passed the liquid crystal display 79, the beams are incident on redirecting mirror 81 and then on a further redirecting mirror 41a arranged above the objective lens 3a such that they traverse the objective lens 3a and converge towards the object plane 7a. The central beam consisting of red light forms the retroillumination light beam 43a, and a diameter and a position of the beam in the object plane, 7a are chosen such that the beam enters the eye 31a under surgery through the pupil 32a of the eye for illuminating the retina of the eye and generating a red reflex at the retina. The beam surrounding the beam 43a and consisting of white light constitutes the beam of standard illumination light 45a for the usual illumination of the object plane 7a.

Further, for taking an image with a camera 67a, a semitransparent mirror 63a couples a further partial ray bundle out of a partial beam 20a of a ray bundle 20a on the image side above the objective lens 3a. A controller 61a analyzes the captured image with regard to an optimization of the red reflex. The controller 61a drives the liquid crystal display 79 to adapt the position and the diameter of the central region 73 such that the red light beam 43a transmitted by the central region 73 is matched to the shape of the pupil 32a. Thus, the generation of the red reflex is optimized. The light beam 43a enters the eye through the whole cross section of the pupil or a portion of the cross section of the pupil.

Figure 2:
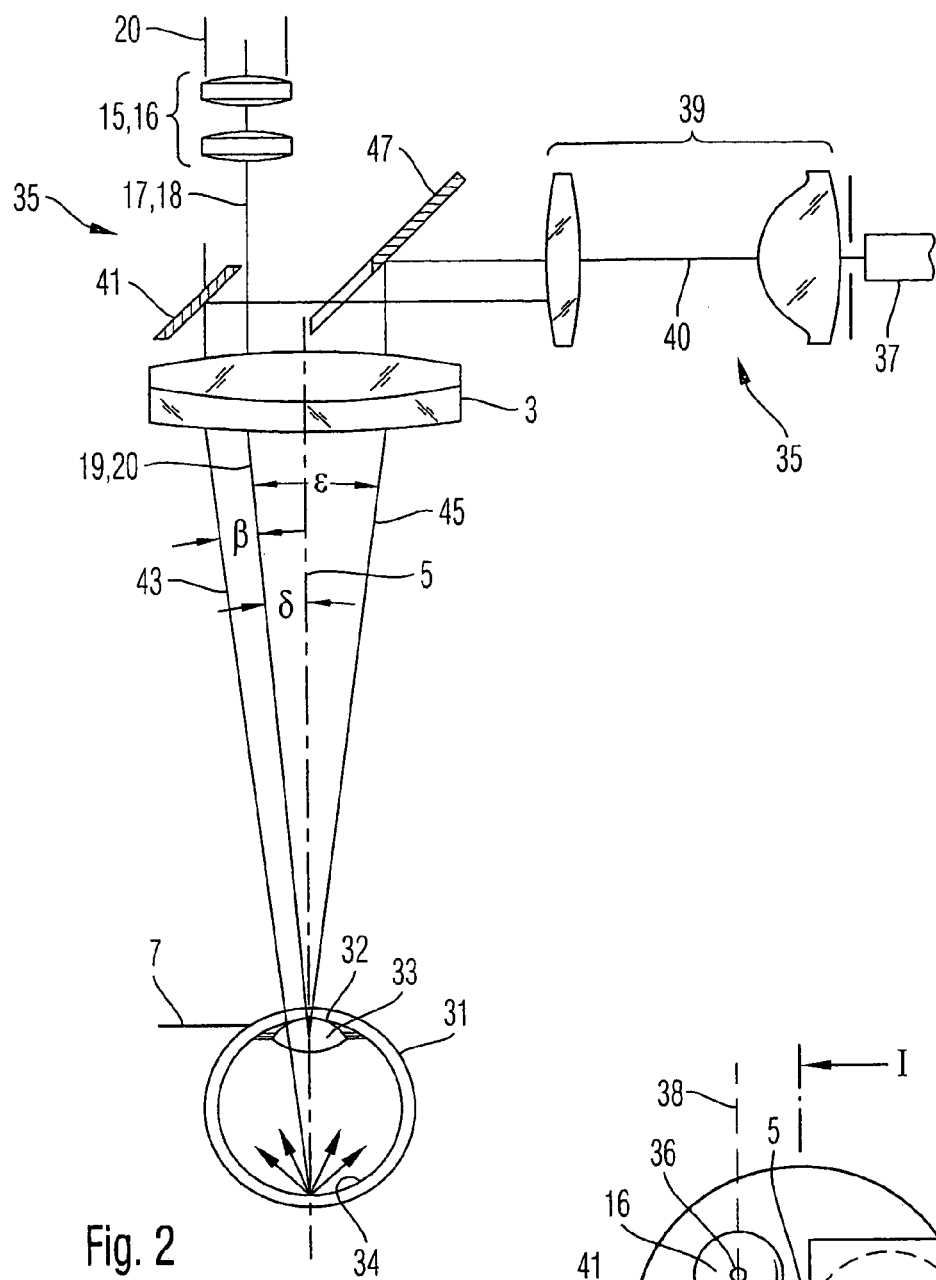
Figure 3:
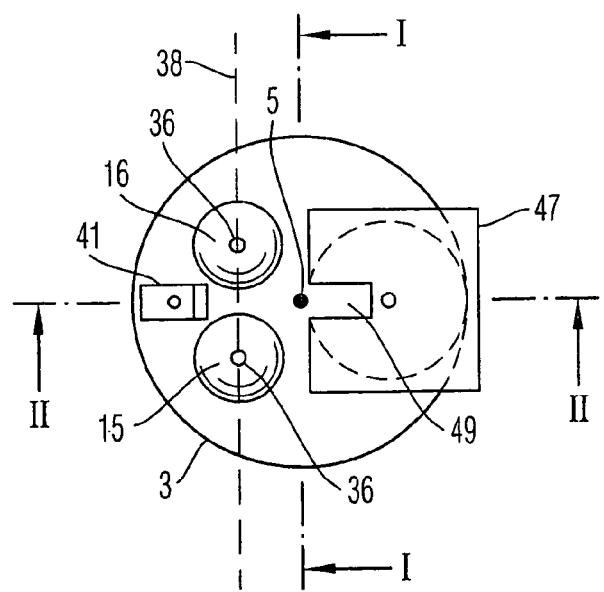

A microscopy system for eye surgery 1b, shown in FIG. 7, has a similar structure as the conventional system, explained with reference to FIGS. 1 to 3. Thus, the microscopy system for eye surgery 1b comprises an objective lens 3b with an object plane 7b and zoom systems 16b, wherein a partial ray bundle is extracted by a beam splitter 63b from a ray bundle 20b traversing the zoom system 16b. The partial ray bundle is directed onto a camera 67b for detecting an image of the object plane 7b to be analyzed by a controller 61b.

The illumination system 35b generates a beam of retroillumination light 43b and a beam of standard illumination light 45b. A white light source 93 and a collimator 94 generate the beam of standard illumination light 45b, and a mirror 47b above the objective lens 3b couples the beam of standard illumination light into the beam path of the objective lens. The objective lens 3b redirects the beam of standard illumination light 45 such that the main ray of the beam extends under an angle ε of about 7° with respect to a plane of main rays of the observation ray bundles 19b, 20b. A blade 87 partially covers the mirror 47b partially for changing an intensity of the beam of standard illumination light 45b. An actuator 89 is provided to displace the blade 87 within the plane of the mirror 47b. The controller 61b controls a driver 91 which drives the actuator 89.

Figure 7:
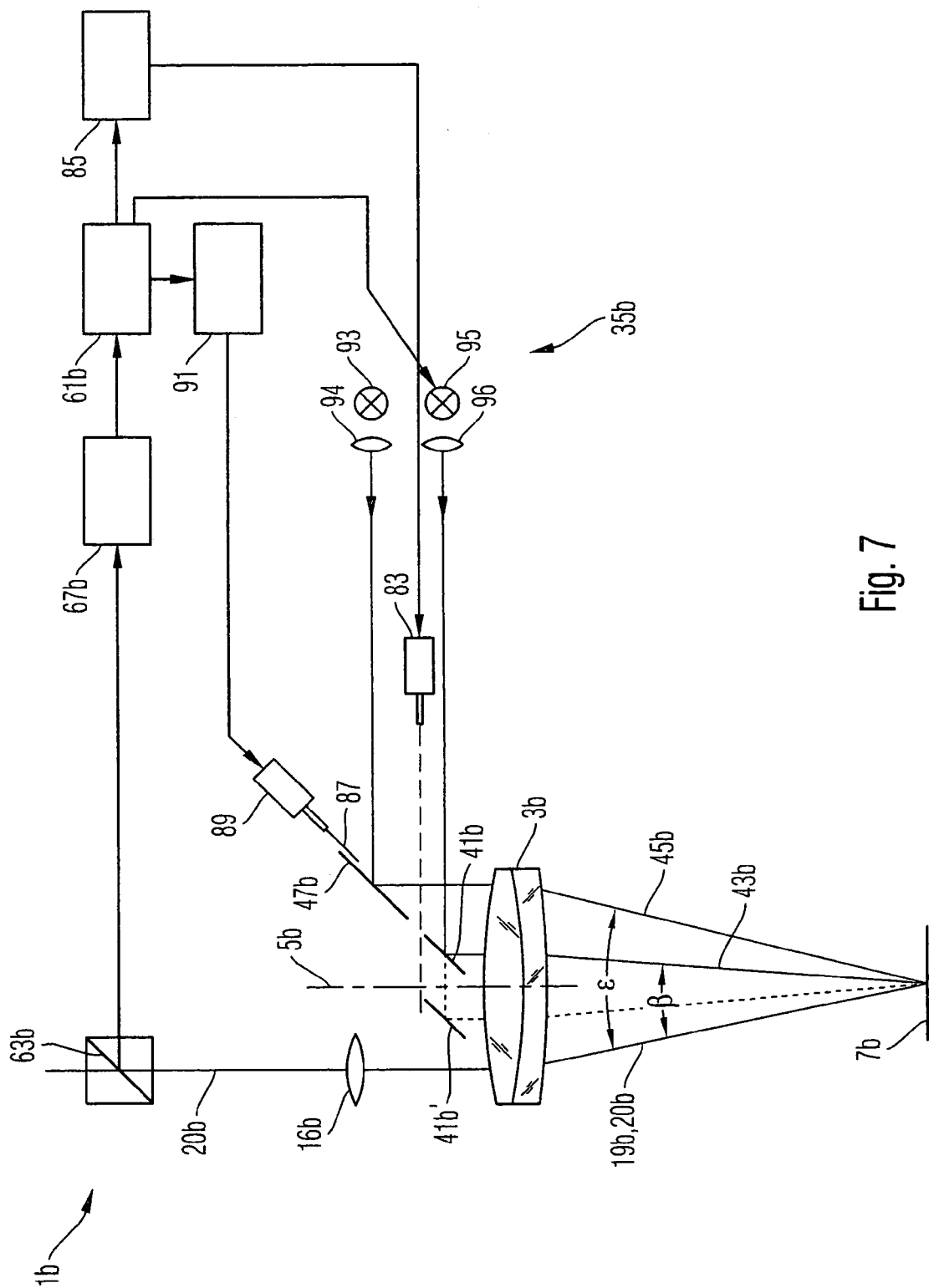
FIG. 7 shows a schematic representation of a microscopy system for eye surgery according to a third embodiment of the invention.

As an alternative to the embodiment shown in FIG. 7, the beam of standard illumination light 45b may also be controlled by an LCD device or a DMD device in order to adjust the color and intensity of the beam 45b. It is also possible to form the beam of standard illumination light such that substantially no light intensity enters the pupil of the eye; details thereof have been explained in the context of the embodiment shown in FIG. 6.

A light source 95 and a collimating lens 96 generate a beam of retroillumination light 43b, and a mirror 41b above the objective lens 3b couples the beam into the beam path of the objective lens. An actuator 83 is provided to displace the mirror 41b between different locations and transverse to an optical axis 5b of the objective lens 3b wherein FIG. 7 shows two of the locations or positions of the mirror 41b. However, the actuator 83 can displace the mirror continuously between the two locations shown in FIG. 7 in order to change an angle β within a range from −2° to 2°, the angle β being the angle between a main ray of the beam of retroillumination light 43b and the plane of the observation ray bundles 19b, 20b. The controller 61b controls a driver 85, which drives the actuator 83.

Although it is not shown in FIG. 7 for reasons of clarity, it is also possible to assign a displaceable blade to the mirror 41b for partially covering the mirror 41b in a controllable manner to change an intensity of the beam of retroillumination light 43b.

Alternatively or in addition to the mirror 41b, an LCD or a DMD may be provided to form the beam of retroillumination light 43b with regard to at least one of its color and its shape, i.e. particularly its diameter, when entering the pupil. Thus, it is possible that substantially no intensity of the beam of retroillumination light 43b is incident on a periphery of the pupil, and thus substantially its entire intensity enters the pupil and herewith the eye.

If the red reflex decreases during the surgical treatment as a result of a displacement of the eye or of another reason, the controller 61b detects this by analyzing the image captured by the camera 67a and changes the position of the redirecting mirror 41b with regard to an optimization of the red reflex.

The following method may be employed:

The controller 61b determines the dominating colors within a central region of the image captured by the camera 67b. If the red reflex is satisfactory, the intensities I of the individual colors fulfill following relations:

$$I(red) > I(green) > I(blue)$$

and $$\frac{I(red)}{I(blue)} > \frac{I(red)}{I(green)} > \frac{I(green)}{I(blue)}.$$

In order to determine a movement direction of the actuator resulting in an improvement of the red reflex, the controller may start to actuate the actuator 83 at first in one arbitrary direction, and determine whether the result is improving, i.e. whether, for example, a ratio I(red) over I(blue) increases relative to a ratio I(red) over I(green). If this is the case, the movement is carried on in this direction; otherwise the actuator 83 is actuated into the opposite direction. This method may be continued, until a position is found for the mirror 41b at which the above-mentioned relations for the red reflex are optimized.

A red reflex, generated by a not quite optimal position of the mirror 41b has, among others, the property that a luminous intensity within the pupil and detected by the camera 67b is not arranged symmetrically with respect to a center of the pupil. In particular, this may result in a somehow crescent-shaped illumination of the pupil by the retroillumination light. The controller 61b may analyze this asymmetry in the image and may directly derive the movement direction for the actuator with regard to an optimization of the red reflex.

For localizing the red reflex within an image captured by the camera the following method may be employed.

At first those pixels of the image are marked which fulfill an appropriate color condition, for example the above-mentioned color conditions. Herein, also pixels are marked which are not arranged within the pupil and therefore do not contribute to the red reflex. For example, blood vessels arranged outside the pupil, and the like, may also fulfill the color condition.

On the other hand, it may happen that pixels, arranged within the pupil and within the region of the red reflex, do not fulfill the color condition. It is possible to process the image with the markings made therein by an algorithm, which combines areas with marked pixels, for example in such a manner that an unmarked pixel which is arranged between two adjacent marked pixels is also marked. In the same way unmarked pixels which are arranged at a distance to and in-between two marked pixels are also marked. This process may be repeated several times. By this procedure the contiguous marked areas in the image grow. Subsequently, a further algorithm may determine the largest contiguous marked area in the image and those contiguous marked areas which are not connected to the largest contiguous area may be deleted, i.e. the markings of these pixels are cancelled. What remains is one contiguously marked area of the image which can be assigned to the red reflex with high probability. Then the controller may analyze the shape of this contiguous marked area, and the controller may then further act on parameters of the retroillumination system to optimize the shape of the contiguous marked area towards a shape similar to a circular area.

As an alternative to the use of the camera 67b, it is also possible to use only a single color sensor which, in contrast to the camera, does not provide location-dependent information about the image. The color sensor has a sensibility for the three colors and may also provide color signals, as it has been explained above for the central region of the image captured by the camera.

To increase a sensitivity of such process, the controller 61b may modulate the light intensity emitted by the red light source 95. Accordingly, the color signal detected by the camera 67b or the color sensor is also modulated in time, as far as it represents the red reflex. For the detection of the red reflex, the characteristic modulation frequency can be filtered out in order to increase the sensitivity, in particular when using the color sensor. A further improvement of the intensity or selectivity can be achieved, if a lock-in signal detection method is employed at the color sensor. Therein the light source 95 is preferably modulated in synchronized phase with the detection at the color sensor. The modulation frequency may be selected high enough to avoid observation of the resulting intensity variation by the human eye while looking through the microscope. A modulation below 100% is sufficient. Thus, it is for example sufficient to control the modulation of the retroillumination light to 10% of the average intensity.

Further, the controller may drive the actuator 89 via the driver 91 such that a portion of the beam of standard illumination light 45b is within an optimized ratio to the illumination beam for the red reflex. Thereby, it can be achieved that an increase or improvement of the contrast with regard to the red reflex is sufficient for the illumination of the remaining field. As an alternative or supplement, it is also possible to improve the image processing by modulating the intensities of the source 93, as it has been explained before.

Figure 8:
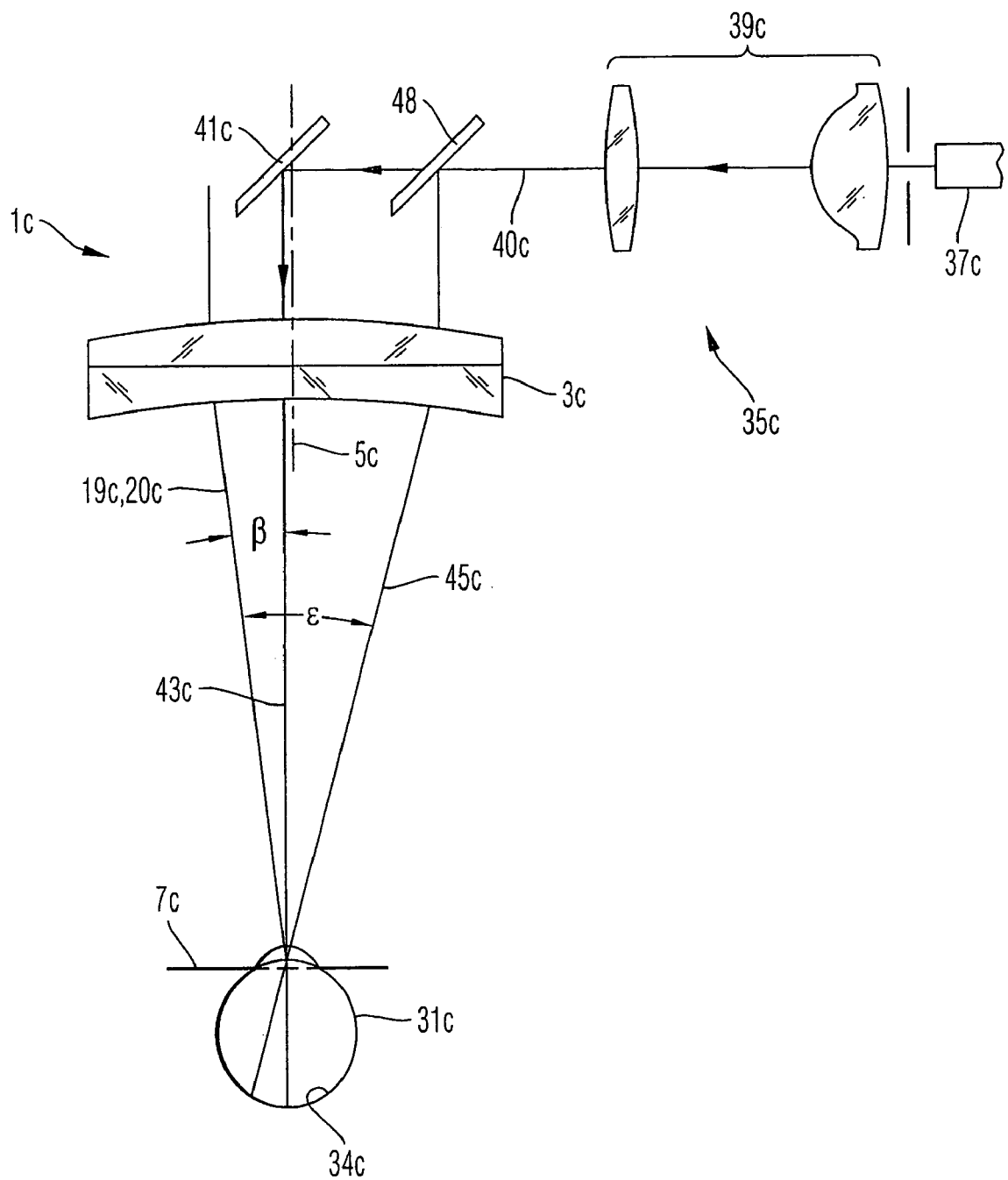
FIG. 8 shows a schematic representation of a microscopy system for eye surgery according to a fourth embodiment of the invention.

A microscopy system for eye surgery 1c, shown in FIG. 8, provides a similar set-up as the conventional system explained with reference to the FIGS. 1 to 3. An optical fiber 37c supplies white light, using a collimating optics 39c. From a collimated light beam 40c a beam of retroillumination light 43c and a beam of standard illumination light 45c are coupled into a beam path above an objective lens 3c. A wavelength-selective beam splitter 48 is arranged within the beam 40c generated by the collimating optics 39c. The beam splitter 48 transmits red light and redirects the remaining light such that it is incident on the objective lens 3c in parallel to the optical axis 5c for forming a beam of standard illumination light 45c. A redirecting mirror 41c redirects the red light traversing the wavelength-selective beam splitter 47c such that it is also incident on the objective lens 3c in parallel to the optical axis, and to form a beam of retroillumination light 43c. A main ray of the beam of retroillumination light is converging onto the object plane 7c under an angle β of about 0° to 2° with respect to the plane of main rays of the observation ray bundles 19c, 20c, whereas the beam 45c and the plane of main rays of the observation ray bundles 19c, 20c enclose an angle ε of about 7°.

The illumination beams 43c and 45c intersect at the object plane 7c.

Here, too, it is possible to displace mirror 41c transverse to the optical axis 5c by an actuator with regard to an optimization of the red reflex.

Figures 9, 10:
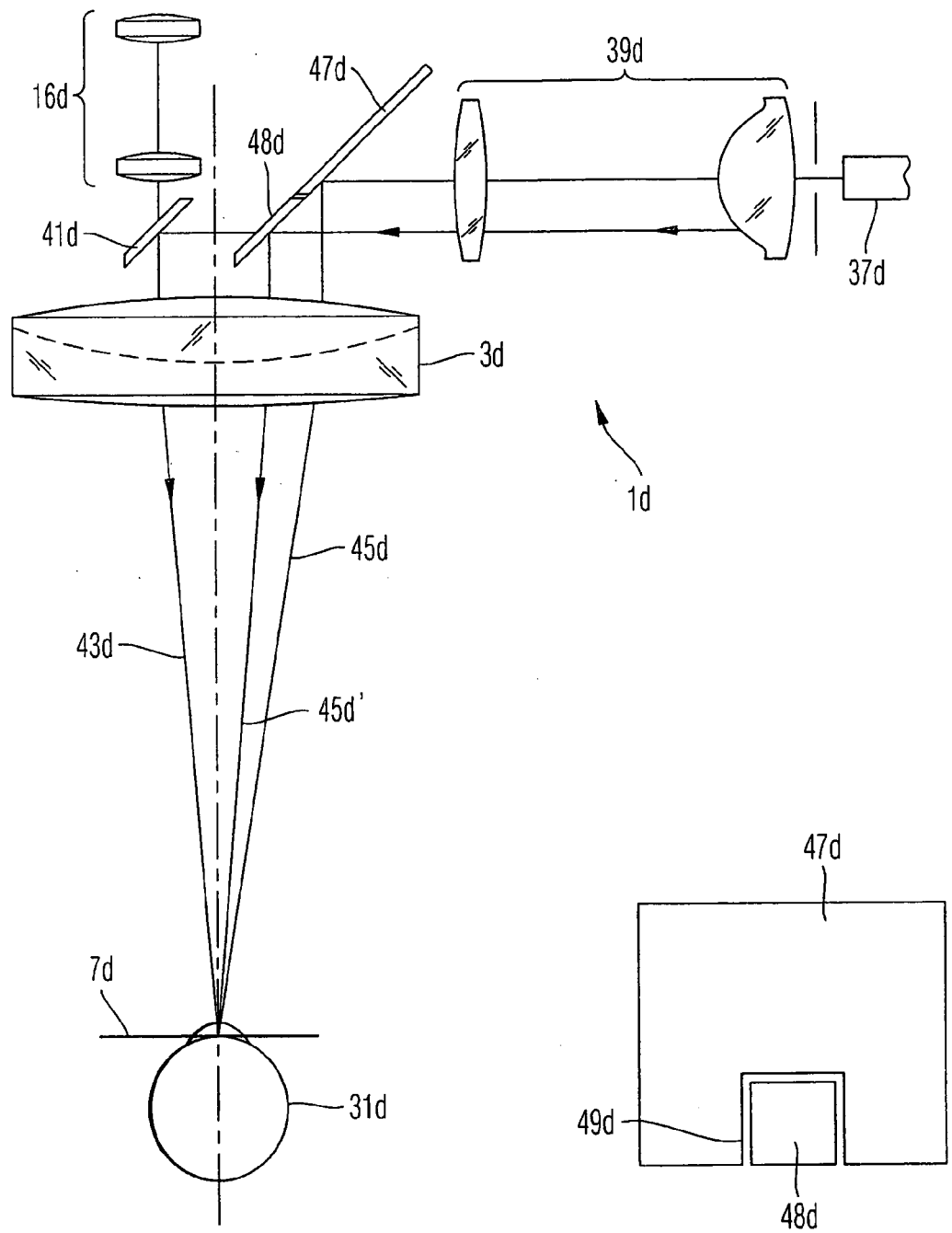
FIGS. 9, 10 show schematic representations of a microscopy system for eye surgery according to a fifth embodiment of the invention.

FIG. 9 schematically shows a variant of the microscopy system for eye surgery shown in FIG. 8. In contrast thereto, a wavelength-selective beam splitter 48d is only provided in a cutout portion 49d of a mirror 47d, shown in FIG. 10, to transmit red light which is coupled into the beam path of the system 1d by a mirror 41d disposed above an objective lens 3d to form a beam of retroillumination light 43d. The beam splitter 48d reflects a partial beam, which forms a partial beam 45d' of a standard illumination, while the mirror 47d surrounding the beam splitter 48d couples a main partial beam 45d of the standard illumination into the beam path.

Figure 11:
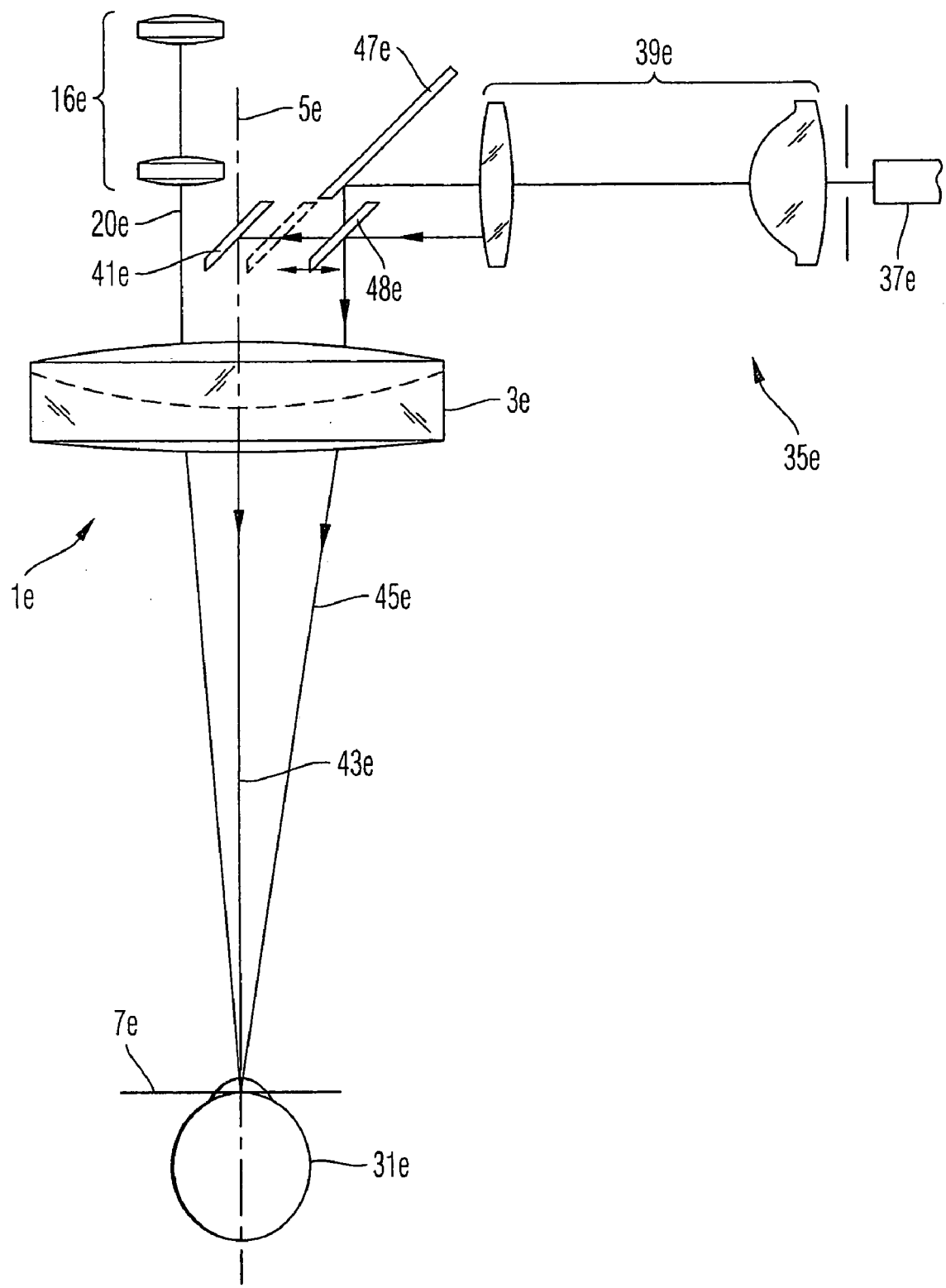
FIG. 11 shows a schematic representation of a microscopy system for eye surgery according to a sixth embodiment of the invention.

FIG. 11 shows a further variant of the microscopy system for eye surgery shown in FIG. 9 and is different therefrom in that the wavelength-selective beam splitter 48e is displaceable transverse to an optical axis 5e of an objective lens 3e, for varying intensities of a beam of retroillumination light 43e and a beam of standard illumination light 45e relatively to each other.

Figure 12:
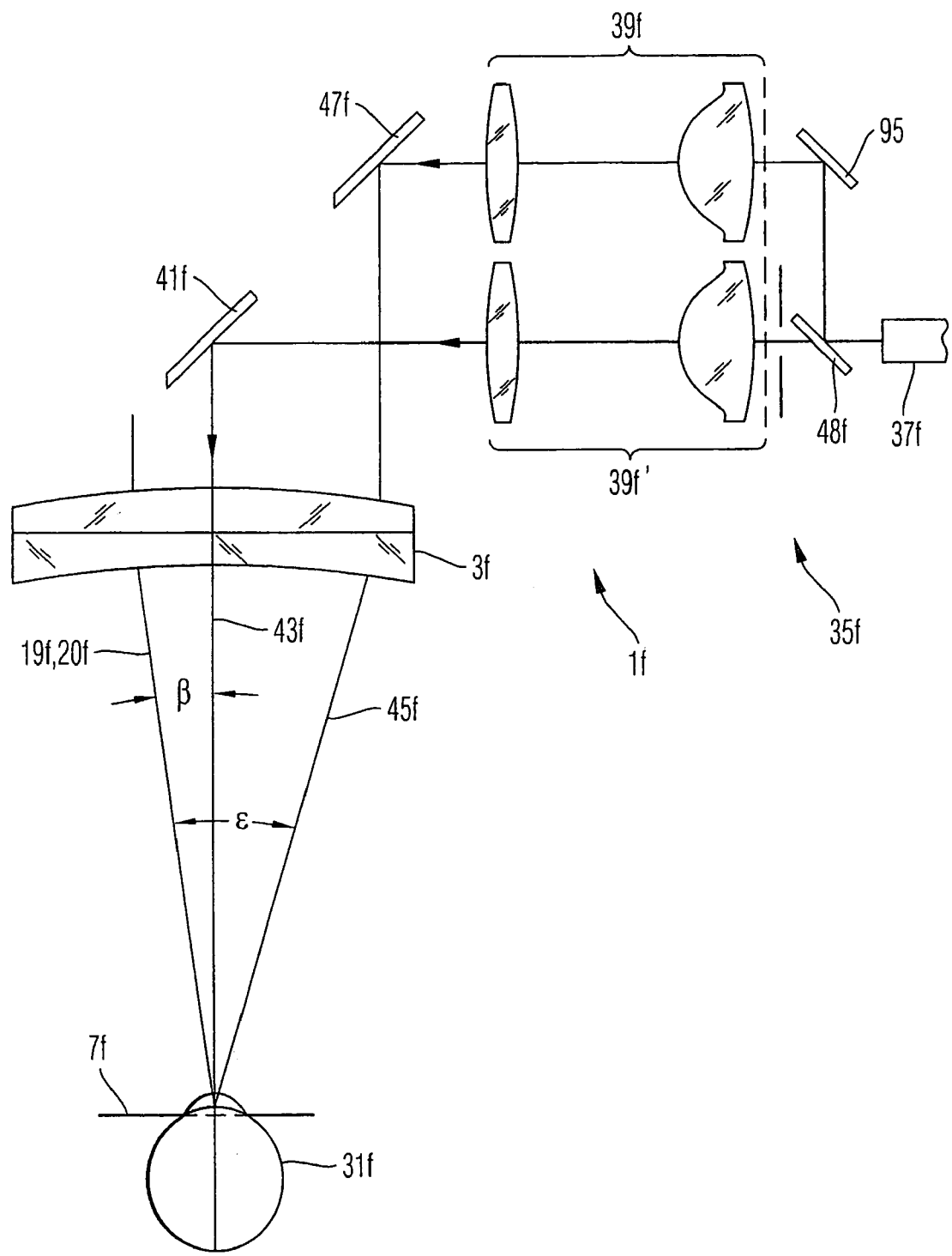
FIG. 12 shows a schematic representation of a microscopy system for eye surgery according to a seventh embodiment of the invention.

FIG. 12 shows a further variant of the microscopy systems for eye surgery shown in FIGS. 8 and 11. Also in the system 1f shown in FIG. 12, a wavelength-selective beam splitter generates, within an illumination system 35f, a beam 43f of retroillumination light and a beam 45f of standard illumination light. A wavelength-selective beam splitter 48f is arranged at an end of an optical fiber 37f which supplies white light to the illumination system 35f. The beam splitter 48f transmits red light which is collimated by a collimating optics 39f. A mirror 41f above an objective lens 3f couples the light into a beam path of the system, for forming a beam of retroillumination light 43f having a main ray which extends towards the object plane 7f under an angle β of 0° to 2° with respect to a plane of main rays of observation ray bundles 19f, 20f. A mirror 95 redirects the partial beam reflected by the wavelength-selective beam splitter 48f, and a collimating optics 39f' collimates this beam. A mirror 47f redirects the collimated beam to a direction parallel to an optical axis of the objective lens 3f and forms a beam 45f of standard illumination light having a main ray extending under an angle ε of about 7° with respect to the plane of main rays of the observation ray bundles 19f, 20f towards the object plane 7f.

Figure 13:
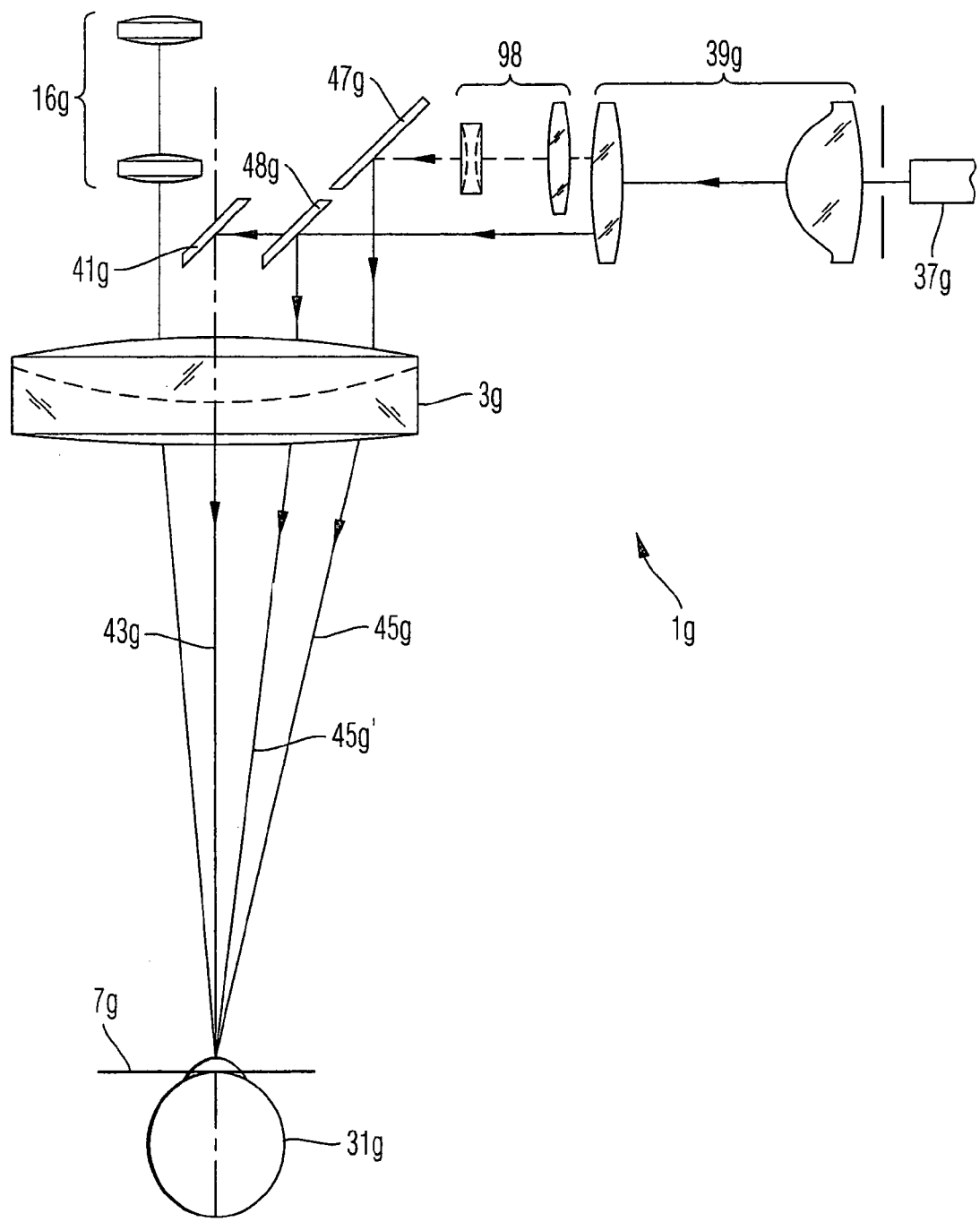
FIG. 13 shows a schematic representation of a microscopy system for eye surgery according to an eighth embodiment of the invention.

A microscopy system for eye surgery 1g shown in FIG. 13 has a similar configuration as the system shown in FIG. 9. A wavelength-selective beam splitter 48g generates a beam 43g of retroillumination light and a beam 45g' of standard illumination light. An additional beam 45g of standard illumination light is reflected at a mirror 47g, wherein a main ray of the additional beam 45g of standard illumination light is incident on the object plane 7g under a greater angle with respect to the optical axis than a main ray of the beam 45g', of standard illumination light. A variable optics 98 is provided in the beam path of the normal illumination beam 45g for changing a size of a region in the object plane 7g which is illuminated by the illumination beam 45g.

Figure 14:
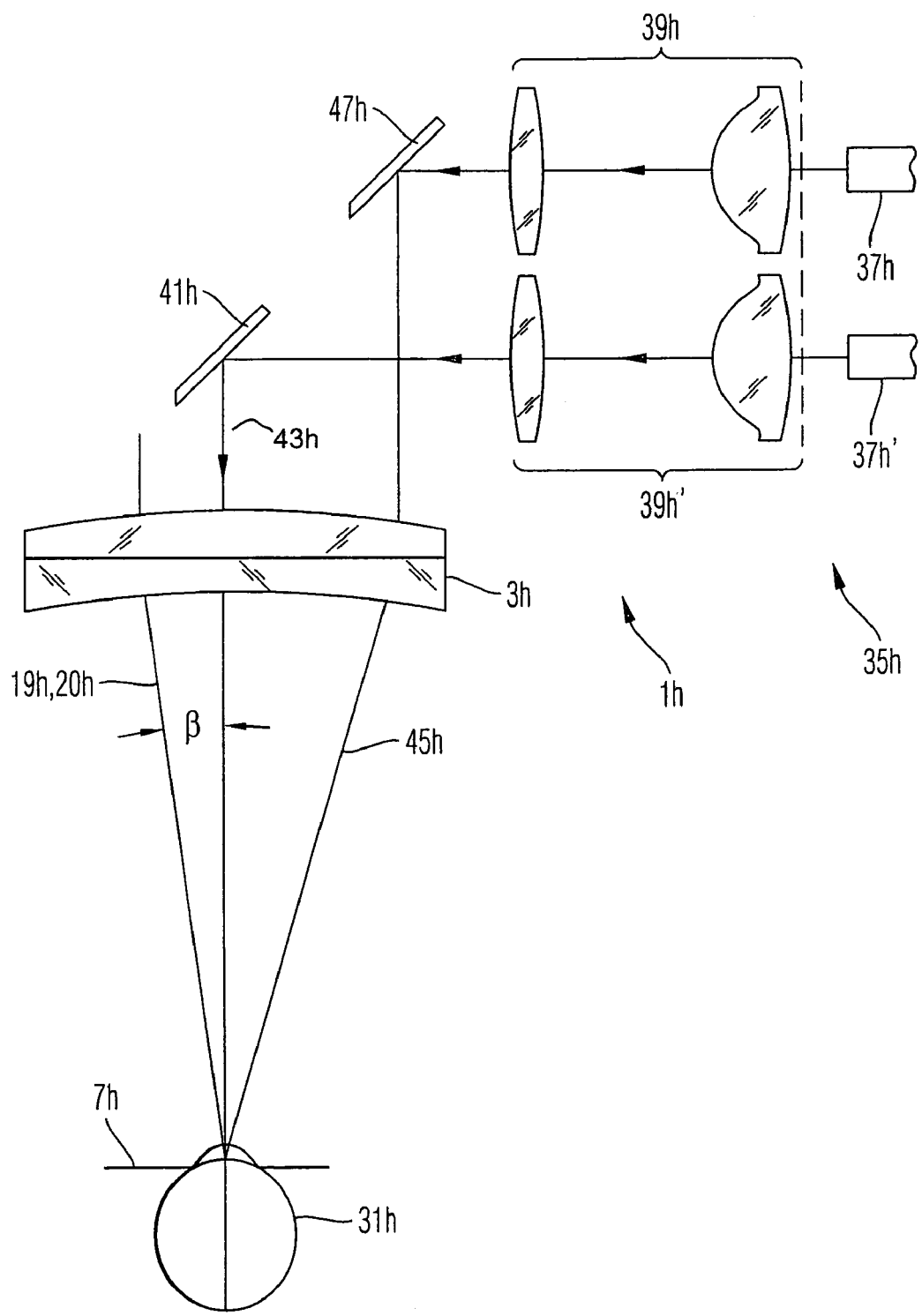
FIG. 14 shows a schematic representation of a microscopy system for eye surgery according to a ninth embodiment of the invention.

A microscopy system for eye surgery 1h shown in FIG. 14 has a similar configuration as the system shown in FIG. 11. However, a beam 43h of retroillumination light and a beam 45h of standard illumination light are not generated by a wavelength-sensitive beam splitter, but by light sources of different colors, which supply their generated light via two separate optical fibers 37h and 37h' to an illumination system 35h. The optical fiber 37h' supplies red light which is collimated by a collimating optics 39h', and coupled into a beam path of the system via a mirror 41h above an objective lens 3h, for generating the beam 43h of retroillumination light having a main ray extending under a small angle β of 0° to 2° with respect to a plane of main rays of the observation ray bundles 19h, 20h. The optical fiber 37h supplies green and blue light, i.e., it supplies the remaining visible spectrum other than red light, which is collimated by a collimating optics 37h and coupled into the beam path via a mirror 47h to generate a beam of standard illumination light 45h, whose main ray extends under an angle ε of about 7° with respect to the plane of main rays of the observation ray bundles 19h, 20h to supplement the beam of retroillumination light 43h to a white light.

Figures 15, 16:
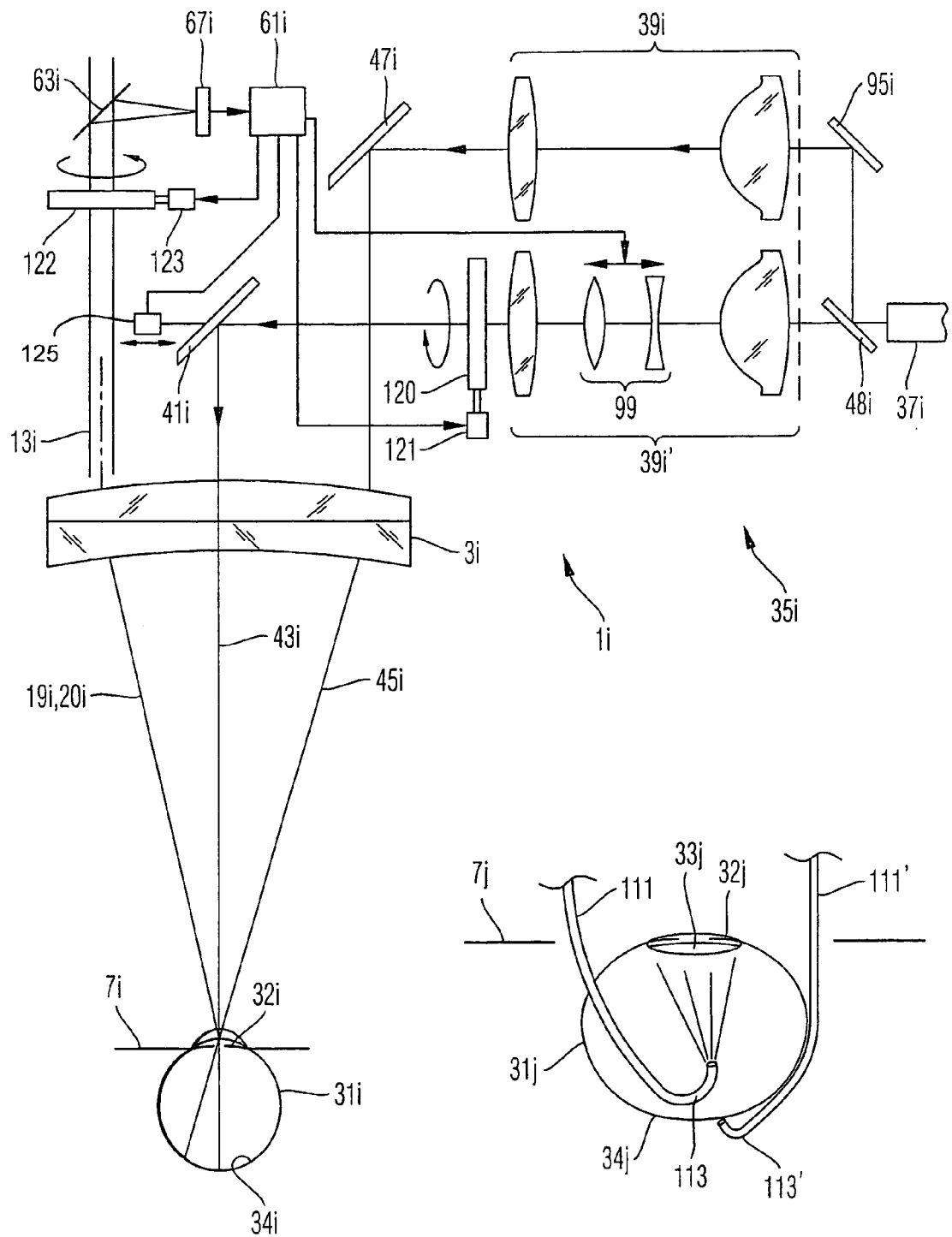
FIG. 15 shows a schematic representation of a microscopy system for eye surgery according to a tenth embodiment of the invention.
FIGS. 16, 17 each shows schematic representations of further variants of a microscopy system for eye surgery.

A microscopy system for eye surgery 1i shown in FIG. 15 has a similar configuration as the system shown in FIG. 11. However, in this case a collimating optics 39i' for a beam of retroillumination light 43i comprises two lens groups 99 which are displaceable along their optical axes to change a convergence or divergence of the beam 43i of retroillumination light. Thereby, it is possible to collimate the beam of retroillumination light 43i such that it is precisely focused on the retina 34i of an eye 31i under surgery to generate an improved contrast-rich red reflex retroillumination in an object plane 7i at an region of the pupil of the eye 31i.

Further, a polarizer 120 is arranged in the beam path of the beam 43i of retroillumination light. The polarizer 120 is rotatable about the beam axis by an actuator 121 controlled by a controller 61i. Thereby, it is possible to provide an optimized polarization for the beam 43i of retroillumination light.

For further improving an appearance of the red reflex within each of the ray bundles 19i, 20i a further polarizer 122, having a function of an analyzer, is disposed in a beam path of the observation ray bundles 19i, 20i and actuated by an actuator 123 which is also controlled by the controller 61i. The polarizer 122 is rotatable about axes of the ray bundles 19i, 20i by the actuator 123, and by an adjustment of the orientations of the polarizers 121 and 122 an optimized appearance of the red reflex is possible. Further, to reduce the thermal stress on the retina 34i at the illuminated locations, the microscopy system for eye surgery 1i, shown in FIG. 15, can be operated such that the luminous spot, generated on the retina 34i by the beam of retroillumination light 43i, is moved back and forth periodically. For this purpose, a scanning mirror 41i may be, for example, displaced or pivoted.

Herein, a luminous spot, generated by the beam of retroillumination light 45i on the retina 34i, has a diameter as small as possible, for example, a diameter of less than 1.5 mm. Only a maximum illumination stress tolerable for the retina 34i limits a smallest diameter of the luminous spot, and as a result thereof, same depends also on the intensity of the beam of retroillumination light 45i.

The displacement of optical elements 99 is controlled by a controller 61i which evaluates an image of the object plane 7i captured by a camera 67i. Then the evaluation and the drive of the collimation optic are performed to optimize the quality of the red reflex retroillumination.

For executing an optimization method as described in the following, a mirror 41i is displaceable to change or scan the location where the beam 43i is incident on the retina 34i. At first, the controller 61i adjusts the position of the mirror 41i via an actuator 125 such that a visible shadow border is visible in the image within a central region of the pupil 32i of the eye 31i. Then an actuator for displacing elements 99 is actuated until the shadow border appears with a maximum contrast in the image captured by the camera 67i. Then the beam of retroillumination light 43i is focused onto a very small spot on the retina 34i of the eye 31i, and herewith, a substantially optimal adjustment of the convergence of the beam of retroillumination light 43i has been found. Then the controller 61i restores the position of the mirror 41i such that the red reflex retroillumination illuminates the pupil 32i of the eye homogeneously. Herein, the displacement of the mirror is not restricted to translational displacement and may also comprise a rotation, a transverse motion or a tilt.

Figure 17:
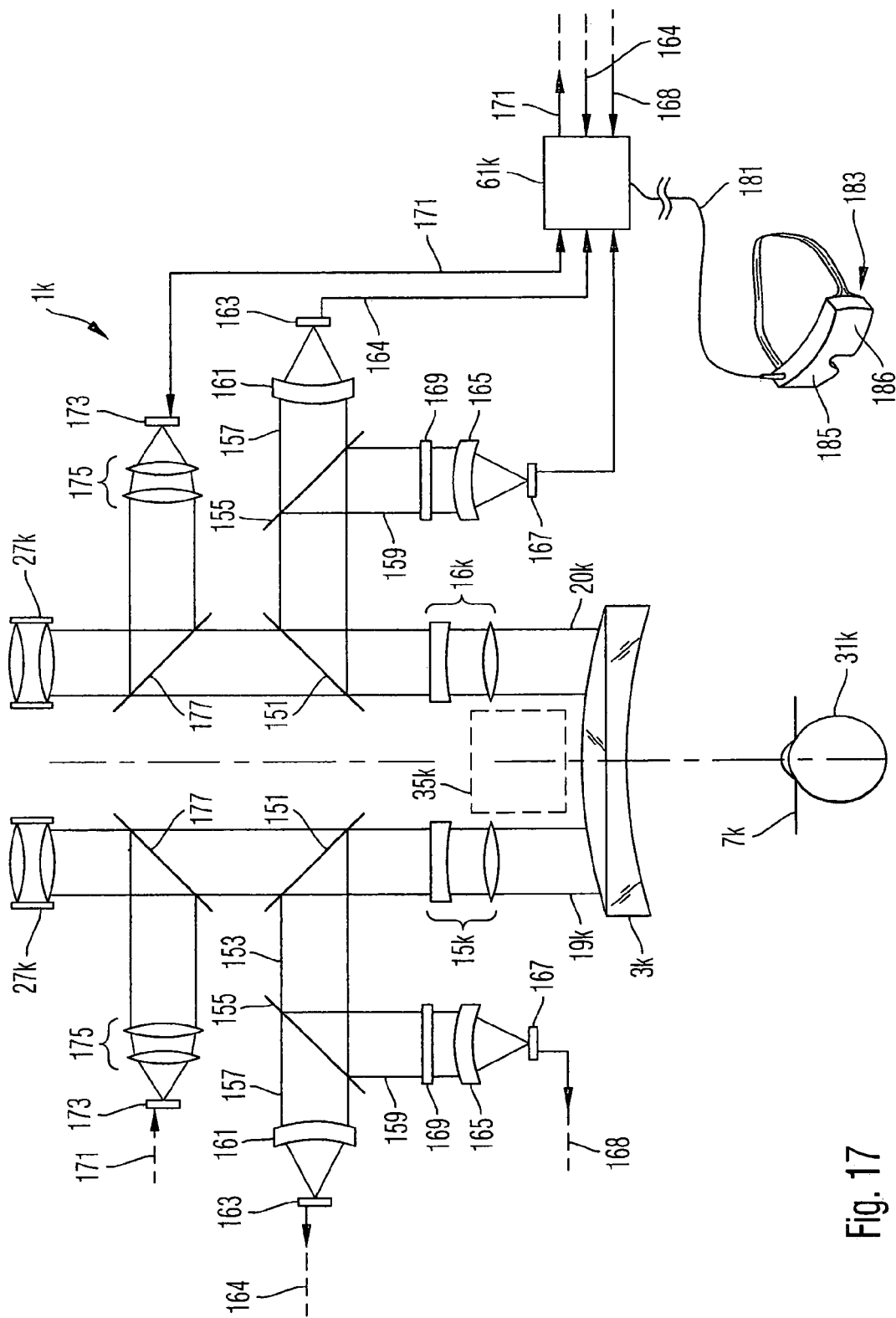

FIG. 17 schematically shows a further embodiment of a microscopy system for eye surgery 1k in accordance with the present invention. This system comprises a microscopy optics having an objective lens 3k and an illumination system which is shown in FIG. 17 schematically only as a block 35k. The illumination system 35k generates, among others, a beam of retroillumination light for observation of a red reflex of an eye 31k and can have a configuration and a function as illustrated above with reference to the illumination systems shown in FIGS. 4 to 15.

Firstly, the observation of the examined eye 31k is performed via oculars 27k of the microscopy system, the oculars being supplied with light in form of a left partial ray bundle 19k and a right partial ray bundle 20k via zoom systems 15k and 16k, respectively.

In the left partial ray bundle 19k, a beam splitter 151 is provided for coupling out a beam 153 which is split by a further beam splitter 155 into further partial beams 157 and 159. A camera optics 161 is provided in the beam 157 such that the camera 163 may detect an image of the object plane 7k. Image data, produced by the camera 163, are supplied to a controller 61k via a data line 164. The partial beam 159 is also supplied to a camera optics 165 of a further camera 167 such that it can detect images of the object plane 7k. Image data, produced by the camera 167, are also transmitted to the controller 61k via a data line 168. Herein, a filter 169 is arranged in the beam 159, which has a transmission characteristic adapted to the color of the beam of retroillumination light provided by the illumination system 35k. Thus, the filter 169 substantially blocks wavelengths which are not contained in the beam of retroillumination light. Thus, images captured by camera 167 represent intensity distributions which are mainly caused by the red reflex. These images of possibly weak intensity are amplified and coupled into the beam path of partial beam 19k, whilst the controller 61k transmits the relative image data via a data line 171 to a LCD display 173, which displays the data as images. Then the beam path of beam 19k and the images are merged by a collimation optics 175 and a coupling mirror 177. This is done such that an observer who looks into the left ocular 27k views a direct optical image of the object plane 7k, as it is transported by the beam 19k to the ocular, and he views as an overlay image to the direct image an amplified red reflex image, captured by the camera 167.

The recording of the red reflex images by the camera 167 and its coupling into the beam path by the display 173 has the following benefits: The intensity of the beam of retroillumination light which is to be provided by the illumination system 34k can be decreased so far that the retroillumination light beam does not cause any damage to the retina even if it is focused precisely onto the retina of the eye 31k. Thus it is possible to focus the beam of retroillumination light to a very small spot on the retina for generating a contrast-rich red reflex image. Then, even at low intensity, the camera 167 captures the image with a high quality, and the amplified image is coupled into the beam path 19k. The camera 167 may comprise a light amplifier, such as a multi channel plate or the like.

Further, it is possible to use wavelengths for the beam of retroillumination light which the human eye cannot or can only barely perceive. These are, for example, wavelengths of the near infrared or the infrared. If the camera 167 is sensitive for these wavelengths, the camera 167 can thus detect intensity images at these wavelengths. The controller 61k translates the relative image data into a color perceivable by the human eye, for example a green color, and then the image data are displayed on the display 173, as, for example, green images. It has been found that the retina of the human eye has a high reflectivity in the near infrared and the infrared qualifying this kind of light as being appropriate for a retroillumination.

Also in the right partial ray bundle 20k beam splitters 151 and 177 are arranged to couple out a partial beam to be supplied to cameras 163 and 167, and to couple into the ray bundle 20k images generated by a further LCD display 173. The arrangement of the cameras 167, 163 and the display 173 and of the corresponding optical components for the right partial ray bundle 20k is symmetrical with respect to the arrangement of the left partial ray bundle 19k, explained before. The observer, who looks into the oculars 27k, thus perceives a stereoscopic image of the red reflex image.

The cameras 163 are standard light cameras and serve to detect images from the object plane 7k which correspond to the images which an observer receives, when looking directly into the oculars 27k. However, the images captured by the cameras 163 or their image data are transmitted from the controller 61k to a head-mounted display 183 via a data line 181 and are displayed on screens thereof, integrated into the display device 183, as is schematically shown in FIG. 17 with reference number 185 for the left eye of the observer and reference number 186 for the right eye of the observer.

Thereby the observer, carrying the display unit 183 and having no opportunity to look directly into the oculars 27k also perceives a stereoscopic image of the object plane 7k. The controller 61k processes the image data transmitted to the device 183 such that those images represented by the data are merged with those images captured by the cameras 167 and 163. Thus, a user carrying the display unit 183 will also perceive an image of the red reflex in green color for example.

With regard to a further reduction of the thermal stress on the retina of the eye 31k, caused by the beam of retroillumination light, it is possible that the illumination system 35k does not emit the beam of retroillumination light with a uniform intensity, but with a modulated intensity, for example, a pulsed intensity.

Herein, the illumination pulses are synchronized with the integration times of the cameras 167 such that the beam of retroillumination light is substantially switched off, when the cameras 167 are idle, i.e. do not integrate the incident light.

In the above-mentioned examples the illumination beams are either coupled into the beam path by a mirror above the objective lens of the microscopy system, or are generated directly at the objective lens by a light source, without employing a mirror for a redirection such that they are coupled into the beam path of the system directly. These both methods are interchangeable, and in each case a mirror for coupling-in the beam can be substituted by an appropriate light source for directly generating the illumination beam, and vice versa.

It is also possible to supply the illumination beams such that they do not traverse the objective lens, but run aside it in a direction towards the object plane. In particular, incisions or cutouts may be provided in the lenses of the objective lens to allow the illumination beams a free penetration through the objective lens.

FIG. 16 shows a further variant of the retroillumination system. Here, the system comprises an optical fiber 111, which is introduced, for example, through a sclera into the body of the eye up to a vicinity of the retina 34j of the eye. The optical fiber 111 has an end, forming a knee 113 such that it is directed towards the pupil 32j of the eye. Light emitted from the fiber end 113 is then illuminating the pupil and the lens 33j disposed in a region of the pupil 32j, from the backside.

A further variant of such an illumination system is shown in FIG. 16 as optical fiber 111'. The fiber 111' is configured such that it can be introduced along the eyeball and outside of the eye up to a location behind the retina 34j. The optical fiber 111' also has an end 113' forming a knee such that the retina 34j is illuminated from the backside. Then, light traversing the retina 34j illuminates the pupil 32j or the lens 33j from the backside.

In the previous embodiments the object plane has been observed via the oculars supplied with the light originating from the object plane through observation ray bundles 19, 20. However, in the context of the present application, it is provided to observe the object plane not only directly through oculars, but alternatively or auxiliarly to this, also by using a video system, which comprises a camera arranged within an observation beam, and which detects an image, which is displayed to an observer by a display device, such as a still image screen, a head-mounted display or the like.

The filters, used in the previously described embodiments, are each provided as transmission filters. However, it is also possible to realize a filter function corresponding to a transmission filter by a reflective filter. A filter in the sense of the present application may thus comprise a transmission filter and a reflective filter.

An advanced development of the microscopy system for eye surgery comprises a camera, in particular a video camera, and a controller with functions for determining the refractive power data of an eye to be examined or under surgery. The controller determines the refractive power data as at least one of spherical power, cylindrical power, and cylindrical axis, and it outputs the data for displaying them to a user. The controller evaluates information about the position of at least one of the entrance pupils, the adjustment of the observation system, and the adjustment of the illumination system of the microscopy system for eye surgery.

In addition, the microscopy system for eye surgery preferably comprises an actuator, driven by the controller to change at least one adjustment parameter automatically, for example an illumination angle. This can be accomplished by the mirror 41b and the actuator 83, as shown in FIG. 7. The controller preferably comprises an electronic image processing function. For the determination of the refractive power data of an eye various methods may be applied, as described in the following:

According to a first method the controller evaluates a brightness distribution within the pupil of the eye to be examined or under surgery, wherein the evaluation of the brightness distribution is performed according to the method of retinoscopy (sciascopy). The brightness distribution may be a distribution of the brightness of at least one of a red reflex and a distribution in another wavelength range, preferably a wavelength range within the infrared.

According to a second method the controller changes an adjustment of the illumination automatically, wherein for example, an illumination angle within the eye is changed. If the entrance pupil of the illumination system or the image of the entrance pupil, respectively, is not lying on the fundus of the eye, the camera views a light/shadow movement in the pupil of the eye upon variation of the illumination angle. The controller evaluates the speed and the direction of the light/shadow movement and derives therefrom the refractive power data.

A third method employs a controller, varying the position of the entrance pupil of the illumination system by an appropriate adjustment facility with an actuator until the image of the entrance pupil is lying on the fundus. In this case, as known from retinoscopy, a "flickering" of the pupil of the eye occurs upon changes of the illumination angle. I.e., no light/shadow border, which moves through the pupil, is visible any more, but only a uniform brightening-up or darkening of the whole pupil. The controller follows up the adjustments, made at the illumination system and initiated by the controller, to achieve this state. The controller uses this information to determine the refractive power data of the eye.

For all variants of these methods it is preferable to realize the illumination as a slit illumination such that the slit illumination may be oriented towards at least two different directions, being traverse to the optical axis, to measure a directional dependency of the refractive power data of the eye.

Summarized, a microscopy system for eye surgery with an objective lens is suggested, which provides a retroillumination system to generate a so-called red reflex illumination during an eye-surgical treatment, in particular during a cataract operation.

While the invention has been described also with respect to certain specific embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A microscopy system for eye surgery, the microscopy system comprising:
    an objective lens for imaging an object plane of the objective lens;
    a retroillumination system for generating at least one beam of retroillumination light directed towards the object plane from an objective lens side of the object plane wherein said beam of retroillumination light comprises substantially only visible light having wavelengths greater than 540 nanometers; and
    a standard illumination system for generating a standard illumination beam directed towards the object plane from the objective lens side of the object plane, wherein an angle between a main ray of the beam of retroillumination light and a main ray of the beam of standard illumination light is greater than 3°.

2. The microscopy system according to claim 1, wherein the beam of retroillumination light comprises substantially only visible light having wavelengths greater than 600 nanometers.

3. The microscopy system according to claim 1, wherein the beam of retroillumination light comprises red light.

4. The microscopy system according to claim 1, wherein the retroillumination system comprises a filter in a beam path of the beam of retroillumination light, wherein the filter is configured to be non-transparent for light other than red light.

5. The microscopy system according to claim 1, wherein the retroillumination system comprises a mirror in a beam path of the beam of retroillumination light, wherein the mirror is configured to reflect substantially only red light.

6. The microscopy system according to claim 1, wherein the retroillumination system comprises a light source emitting substantially only red light.

7. The microscopy system according to claim 6, wherein the light source comprises at least one of a light emitting diode and a semiconductor laser.

8. The microscopy system according to claim 1, wherein the retroillumination system comprises a light source for generating a light beam and a beam splitter for splitting the light beam into a beam of standard illumination light and the beam of retroillumination light such that the beam of standard illumination light is directed towards the object plane from the objective lens side of the object plane.

9. The microscopy system according to claim 1, wherein the main ray of the beam of retroillumination light traverses the object plane under an angle of about 0° to about 40° with respect to an optical axis of the objective lens.

10. The microscopy system according to claim 1, wherein the main ray of the beam of retroillumination light traverses the object plane under an angle of about 1° to about 3° with respect to an optical axis of the objective lens.

11. The microscopy system of claim 1, wherein the main ray of the standard illumination beam traverses the object plane under an angle greater than 6° with respect to the optical axis of the objective lens.

12. The microscopy system according to claim 1, wherein the retroillumination system comprises a light source and a plurality of swichable light valve elements for selectively generating a plurality of beams of retroillumination light.

13. The microscopy system according to claim 1, wherein the retroillumination system comprises a light source and a plurality of switchable mirror elements for selectively generating a plurality of beams of retroillumination light.

14. The microscopy system according to claim 1, wherein a cross section of the beam of retroillumination light is displaceable in a plane disposed in between the objective lens and the object plane.

15. The microscopy system according to claim 1, wherein the retroillumination system comprises a displaceable mirror for reflecting the beam of retroillumination light towards the object plane, and an actuator for changing a distance of the mirror from an optical axis of the objective lens.

16. The microscopy system according to claim 1, wherein the retroillumination system comprises a displaceable light source for generating the beam of retroillumination light, and an actuator for changing a distance of the light source from an optical axis of the objective lens.

17. The microscopy system according to claim 1, further comprising a standard illumination system generating a standard illumination beam for illuminating a region outside of a pupil of the eye under surgery, wherein the standard illumination system comprises a first light forming device configured to shape the standard illumination beam such that substantially no light of the standard illumination beam enters the pupil.

18. The microscopy system according to claim 1, wherein the retroillumination system comprises a second light forming device configured to shape the retroillumination beam such that substantially all light of the beam of retroillumination light enters the pupil.

19. The microscopy system according to claim 1, further comprising
a camera for detecting a red reflex image;
a display for the displaying the detected red reflex image to a user; and
wherein a filter disposed in a beam path between the objective lens and the camera, wherein the filter is transparent substantially only for wavelengths contained in the beam of the retroillumination light.

20. The microscopy system of claim 1, wherein the angle between the main ray of the beam or retroillumination light and the main ray of the beam of standard illumination light is between 5° and 9°.

21. A microscopy system for eye surgery, the microscopy system comprising:
an objective lens for imaging an object plane of the objective lens;
a retroillumination system for generating a beam of retroillumination light directed towards the object plane from an objective lens side of the object plane;
a light sensor for detecting light emerging from the object plane, wherein the light sensor is configured to generate a signal representing a quality of a red reflex generated by the beam of retroillumination light; and
a controller for controlling an actuator configured to change a parameter of the retroillumination system in dependence of the signal representing the quality of the red reflex.

22. The microscopy system according to claim 21, wherein the parameter is an angle between a main ray of the beam of retroillumination light and an optical axis of the objective lens.

23. The microscopy system according to claim 21, wherein the parameter is at least one of a convergence and a polarization of the beam of retroillumination light.

24. The microscopy system according to claim 21, wherein the retroillumination system comprises a first polarizer for changing a polarization of the beam of retroillumination light.

25. The microscopy system according to claim 21, wherein the controller is configured to modulate an intensity of the beam of retroillumination light.

26. A microscopy system for eye surgery, the microscopy system comprising:
an objective lens for imaging an object plane of the objective lens;
a retroillumination system for generating a beam of retroillumination light directed towards the object plane from an objective lens side of the object plane, wherein the retroillumination system comprises a collimator for changing at least one of a convergence and a divergence of the beam of retroillumination light; and
a controller for controlling an actuator coupled to the collimator.

27. A microscopy system for eye surgery, the microscopy system comprising:
an objective lens for imaging an object plane of the objective lens;
a retroillumination system for generating a beam of retroillumination light directed towards the object plane from an objective lens side of the object plane, wherein
the retroillumination system comprises a collimator for changing at least one of a convergence and a divergence of the beam of retroillumination light;
a detector for detecting light emerging from the object plane;
a first control module configured to generate a contrast signal based on an intensity variation across the object plane of the detected emerging light; and
a second control module configured to change the convergence of the beam of retroillumination light in dependence of the generated contrast signal.

28. A retroillumination method for an eye of a patient, the method comprising:
directing a beam of retroillumination light through a pupil of the eye onto a retina of the eye;
detecting an image of an object plane disposed in a region of the pupil of the eye; and
changing an angle of the directed beam of retroillumination light with respect to the pupil of the eye, based on the detected image.

29. A retroillumination method for an eye of a patient, the method comprising:
directing a beam of retroillumination light through a pupil of the eye onto a retina of the eye;
detecting an image of an object plane disposed in a region of the pupil of the eye; and
changing at least one of a convergence and a divergence of the beam of retroillumination light based on the detected image.

30. A microscopy system for eye surgery, the microscopy system comprising:
an objective lens for imaging an object plane of the objective lens;
a retroillumination system for generating at least one beam of retroillumination light directed towards the object plane from an objective lens side of the object plane, wherein the beam of retroillumination light comprises substantially only visible light having wavelengths greater than 540 nanometers; and
a standard illumination system for generating a standard illumination beam directed towards the object plane from the objective lens side of the object plane such that a main ray of the standard illumination beam traverses the object plane under an angle greater than 4° with respect to an optical axis of the objective lens.

* * * * *

UNITED STATES PATENT AND TRADEMARK OFFICE
CERTIFICATE OF CORRECTION

PATENT NO.          : 7,307,785 B2                                    Page 1 of 1
APPLICATION NO.  : 10/768700
DATED                  : December 11, 2007
INVENTOR(S)        : Obrebski It is certified that error appears in the above-identified patent and that said Letters Patent is hereby corrected as shown below:

Title page, (75) Inventors, please change "Bernd Spruck, Moeggilngen (DE)" to --Bernd Spruck, Moegglingen (DE)--.

Col. 1, line 6, please change "both of these applications" to --this application--.

Col. 6, line 31, please delete "s".

Col. 10, line 58, please change "39f" to --39f--.

Col. 15, claim 1, line 67, please change "said" to --the--.

Col. 16, claim 9, line 39, please change "40" to --4--.

Signed and Sealed this

Twenty-first Day of October, 2008

JON W. DUDAS
*Director of the United States Patent and Trademark Office*